United States Patent [19]

Hsia

[11] Patent Number: 4,780,210

[45] Date of Patent: Oct. 25, 1988

[54] TANGENTIAL FLOW AFFINITY ULTRAFILTRATION

[75] Inventor: Jen-Chang Hsia, Concord, Canada

[73] Assignee: Her Majesty the Queen in right of Canada, Ottawa, Canada

[21] Appl. No.: 1,175

[22] Filed: Jan. 7, 1987

[30] Foreign Application Priority Data

Jan. 10, 1986 [GB] United Kingdom ................. 8600582

[51] Int. Cl.⁴ ............................................ B01D 13/00
[52] U.S. Cl. .................................... 210/638; 210/639
[58] Field of Search ............... 210/636, 639, 640, 638; 435/68

[56] References Cited

U.S. PATENT DOCUMENTS

| | | | |
|---|---|---|---|
| 4,089,778 | 5/1978 | Gauger | 210/639 X |
| 4,438,032 | 3/1984 | Golde et al. | 435/68 X |
| 4,579,662 | 4/1986 | Jonsson | 210/636 |

Primary Examiner—Frank Spear
Attorney, Agent, or Firm—Nixon & Vanderhye

[57] ABSTRACT

Biological macromolecules are separated from liquid mixtures in which they are contained, in substantially pure form, by a process involving tangential flow ultrafiltration of the liquid mixture in the presence of an affinity gel which binds selectively to the biological macromolecule to be recovered in pure form, in either the positive affinity absorption mode or the negative affinity absorption mode. Thus a mixture containing the biological macromolecule of interest, such as hemoglobin or (oxy)hemoglobin is first mixed with an affinity gel, such as agarose-ATP, which selectively binds to the hemoglobin or (oxy)hemoglobin and then the liquid is subjected to tangential flow ultrafiltration, so that all components of the mixture except the gel-bond hemoglobin pass through the filter. In a second stage, the gel-bond hemoglobin is treated with a salt solution to displace the hemoglobin from the gel, and then the mixture is passed again over a tangential flow ultrafiltration membrane, so that the pure hemoglobin is separated from the gel, and collected in filtrate. The affinity gel which remains in retentate can then be regenerated and re-used.

14 Claims, 5 Drawing Sheets

TANGENTIAL FLOW AFFINITY ULTRAFILTRATION

This invention relates to purification and separation processes, for recovery and isolation of biochemical macromolecular products from mixtures thereof and from media in which they are contained or in which they have been produced. More particularly, it relates to a process of biochemical purification which combines the processing techniques of affinity chromatography and tangential flow ultrafiltration, and is capable of being operated on a continuous-flow or semi-continuous-flow basis, for use in the purification or separation of molecules of biological interest. The process is particularly suited to the purification of hemoglobin and chemically-modified hemoglobin, but is generally applicable to a wide range of biological and biochemical products.

Several processing techniques exist in the prior art to separate mixtures of molecules of biological interest. One of the most powerful of these is affinity chromatography, an extremely powerful separation method which separates on the basis of specific and selective binding of molecules of interest to an affinity gel. Affinity gels typically comprise a ligand-binding moiety immobilized on a gel support. Many types of well characterized molecular interactions exist which can be exploited in affinity chromatography.

In U.K. patent application, Ser. No. 8,615,675, filed June 26, 1986, and various other patent applications equivalent thereto and filed in other countries, there are described methods for the purification of hemoglobin and its derivatives which have been chemically modified to improve oxygen-carrying and circulatory characteristics. These methods use affinity chromatography and are based upon the fact that native (oxy)hemoglobin binds specifically to polyanionic moieties of certain affinity gels. Contrary to previous beliefs, (oxy)-hemoglobin as well as hemoglobin can be separated by affinity chromatography, according to the aforementioned U.K. patent application. This is a particularly important finding from a practical point of view, since it is virtually impossible to maintain hemoglobin free from (oxy)hemoglobin in anything other than strictly controlled laboratory conditions. This method is applicable to both positive and negative affinity absorption mode. Positive affinity absorption mode is used to purify hemoglobin from various sources, e.g. red blood cell lysates. When a mixture such as a red cell lysate is passed through an affinity gel under conditions favouring hemoglobin binding to the gel, hemoglobin is retained while the other components of the mixture are eluted. Subsequent elution of the retained hemoglobin from the gel yields pure hemoglobin. Negative affinity absorption mode is used to separate modified hemoglobin (i.e. hemoglobin whose polyanion binding site has been chemically modified by the covalent attachment of any of several known substances, for the purpose of ameliorating the undesirable features of hemoglobin solutions as acellular oxygen-carrying fluids) from the residual unmodified hemoglobin which remains due to the incomplete nature of the modification reaction. In this process, unmodified hemoglobin is retained by the affinity gel while modified hemoglobin, which cannot bind to the gel because its polyanion binding site is by definition covalently occupied by the modifying agent, is eluted as the unretained fraction. These methods both employ affinity chromatography columns which are highly specific and, therefore, give very pure products. However, the affinity chromatography is a relatively slow and laborious "batch" process.

Another known separation method is membrane ultrafiltration, which separates compounds on the basis of molecular size. In the simplest form of this process, a solution is poured through a filter with pores of a defined size, and those solutes which are too large to pass through the pores are separated from those which can pass through. This type of filtration is limited, however, by the fact that non-filterable solutes accumulate on the filter and eventually block the flow of fluid through it.

This problem has recently been overcome in a new process known as tangential-flow ultrafiltration (Gabler, F. R., ASM News, Vol. 50 No. 7 (1984), p. 299). In this process, the solution flows parallel to the filter membrane so that the fluid flow continually cleans the filter surface and prevents clogging by non-filterable solutes. A pressure differential across the membrane causes fluid and filterable solutes to flow through the filter. This can be conducted as a continuous-flow process, since the solution is passed repeatedly over the membrance while that fluid which passes through the filter is continually drawn off into a separate circuit. Since it separates solely on the basis of molecular size, however, tangential-flow ultrafiltration lacks the ability of selective separation based on biological specificity such as that used in affinity chromatography.

The present invention involves use of tangential-flow filtration in a "continuous-flow" separation process. In this process, separation of retained and unretained fractions is achieved by differential filtration based upon molecular size. Affinity gel separation is also employed, wherein an affinity gel is placed in the solution or mixture containing the fractions to be separated, on the upstream side of the filter. Since the gel particles are much larger than the solute particles, a filter can be selected which will allow unbound solutes, i.e. solutes not bound to the gel, to pass through the filter, while preventing the passage of gel particles and any substance bound to the gel.

According to the invention, there is provided a process for the separation of molecules of biological interest from a mixture containing said molecules of interest, which comprises subjecting said mixture to tangential flow ultrafiltration in the presence of at least one macromolecular affinity substance which specifically binds said molecules of interest and prevents their filtration while other smaller molecules are removed by filtration.

Also according to the invention, there is provided a process of separating a first biological macromolecule from a second biological macromolecule which comprises treating a mixture containing both of said first and second biological macromolecules with an affinity gel which selectively binds to one of said first and second macromolecules, but not to the other thereof, and subsequently subjecting the mixture containing the affinity gel bound macromolecules to tangential flow ultrafiltration, so as to obtain affinity gel bound macromolecules in the retentate of said ultrafiltration and non-affinity gel bound macromolecules in the filtrate of said ultrafiltration.

The term "biological macromolecule" used herein is intended to mean molecules of at least about 1,000 daltons molecular weight, and of natural biological or biochemical origin, or produced by biological or biochemical processes.

In the preferred form of the present invention, the processes of affinity gel separation and tangential flow ultrafiltration are combined in a novel process called tangential flow affinity ultrafiltration. In this combined process, a liquid solution or mixture containing a component to be isolated is subjected to tangential flow ultrafiltration in the presence of an appropriate affinity gel.

Affinity substances include soluble ligand-binding macromolecules and affinity gels. For the purposes of purifying native and chemically modified hemoglobin, the basis of the affinity property of the gel is the binding of native hemoglobin to the polyanionic moiety of polyanion affinity gels, e.g. ATP-agarose. Isolation of the component of interest is achieved by specifically binding it (a process conventionally known as "positive" affinity chromatography) or by binding other components of the mixture (conventionally known as "negative" affinity chromatography).

A wide variety of affinity gels suitable for use in the present invention are known, and many are commercially available. The nature of the gel, the ligand to be attached to the gel for purposes of binding to the selected biological macromolecule, and the chemical manner of linking the ligand group to the gel must all be chosen with regard to the nature of the selected biological macromolecule, the stability thereof towards the reagents and solutions to which the affinity gel will be subjected in practice of the invention, and the chemical removal of the biological macromolecules from the affinity gel after the tangential flow ultrafiltration has taken place. Since most processes of separation of biological macromolecules take place in aqueous medium, stability of the gel and the ligand-gel linking groups and bonds towards water will normally be important. The ligand group should be chosen to have a high degree of specificity towards the biological macromolecule to be bound to the gel.

In the case where the biological macromolecule is hemoglobin or (oxy)hemoglobin, the affinty gel preferably comprises a polyanionic-molecule linked by a spacer group (cross-linking agent) to an affinity gel by known methods. Examples of polyanionic ligands are diphosphoglycerate, nucleoside phosphates, inositol phosphates and sulphates, etc. In fact, any polyanionic ligand, which is able to bind in the binding site or cleft naturally occupied by DPG in hemoglobin, may be used. A wide variety or these are known to those skilled in the art and published in the relevant scientific literature. They include, in addition to those above, various organic phosphates, diphosphates and polyphosphates, for example pyridoxal phosphate; phosphates of nucleic acids such as ADP, ATP, guanosine phosphates, cytosine phosphates, thymine phosphates, uracil phosphates, etc.; inositol phosphates; carbohydrate phosphates and sulfates; carbohydrate mono- and poly-carboxylates, etc.

The ligand should not bind to the biological macromolecule so strongly that difficulties of elution of the biological macromolecule from the gel are encountered. If the biological macromolecule is too tightly bound, then denaturing reactions may occur in the use of the necessarily strong reagents or conditions for elution, e.g. extreme pH. When using organic polyphosphates as ligands to extract (oxy)hemoglobin, the bond strength of the ligand to the (oxy)hemoglobin appears to increase with increasing numbers of phosphate groups. The optimum bond strength appears to be derived from tri-, tetra- and penta-phosphates, so that preferred ligand-forming compounds are nucleoside tri- and tetraphosphates, such as ATP, inositol tetraphosphate, inositol penta-phosphate and the like, including mixtures thereof. The ligand molecule is chemically bonded to the gel side groups in a manner such that the phosphate, sulphate or carboxylate functional groups are left intact to react with the polyanion binding site in the hemoglobin. In the case of ATP, it can be bound to the gel via its N-6 position or 8-position of adenosine, or through the periodate oxidized ribose moiety, for example.

The chromatographic gel is generally provided with a cross-linking agent or spacer, which is effectively a chemical side chain group covalently linked to the gel at one end and providing a reactive group on the other end for chemical attachment to the ligand compound. While these spacers do not need to be linear chemical groups, they should provide a spacing between the gel backbone and the reactive group for ligand attachment of at least about 5 angstroms, and preferably at least 6 angstroms. In practice, this means that they should contain a minimum of four linearly arranged atoms separating the gel from the functional group. Otherwise, insufficient loading of ligand groups onto the chromatographic gel might occur. The spacer groups should be covalently linked, so that they are not broken during purification, regeneration and sterilization processes. They should be stable and inert to all the components of the mixture to be separated, and to the elution reagents to be used. Examples of suitable reagents to be used to react with the gels to provide suitable spacer groups are adipic acid, diaminohexane and derivatives thereof, such as adipic dihydrazide, and various other, known diacids and diamino compounds.

The choice of suitable chromatographic gel is within the skill of the art, and can be made from various commercially available products, provided that certain basic criteria are observed. The gel needs to be substantially water insoluble, derivatizable and non-toxic. It needs to be able to tolerate the regeneration conditions and processes of treatment, for meeting sterile, sanitary administration for I.V. injection requirements. Thus it must be readily sterilizable without impairment of its chemical properties. Examples of suitable affinity gel supports are agarose and silica gels.

In general, modified cross-linked polysaccharide chromatographic gels are useful, as exemplified by those commercially available from Pharmacia A.S. under the trade names Sephadex, Sepharase, Sephacryl and Suparose. Commercially available chromatographic silica gels and modified silica gels are also suitable. The gels in many cases are available with spacer functional groups already attached. They can be obtained with functional amino, epoxy or hydroxy groups. They may also, in addition, have an appropriate ligand chemically attached to the spacer group, so that they are effectively ready for use in the process of the present invention.

When the process of the invention is used to isolate biological macromolecules other than hemoglobin and modified hemoglobins, a different selection of ligand may be made to ensure its specificity towards the chosen biological macromolecule. Such selections are generally within the skill of the art, based on relevant scientific literature and the properties and characteristics of the specific biological macromolecule. Commonly, the ligands will be biological substances themselves. For example, alpha-fetoprotein from fetal sources is normally partially purified by antibody absorption (see, for example, Nishi, "*Cancer Research*" 30, Oct. 1970, pp. 2507-2513; Ruoslahti, "*J. Immunol*" 121, 1687-1690 (1978); and Parmelee et al., "*J. Biol. Chemistry*" 253 No. 7, Apr. 10, 1978, pp. 2114-2119), but remains contaminated with albumin. The removal of the albumin from alpha-fetoprotein can be accomplished by tangential flow affinity ultrafiltration (TFAU) in the following manner. In this specific case, a biological macromolecule with specific carbohydrate binding specificity, e.g. Concanavalin-A (Con-A) can be linked to a suitable gel and used as affinity gel for the specific separation of the glycoprotein alpha-fetoprotein from the non-glycoprotein albumin, by TFAU in the presence of a Con-A agarose gel. Such a process can form part of the procedure for isolating valuable alpha-fetoprotein from fetal serum and ambiotic fluid (see, for example, Page, *Can. J. Biochem.* 51, 1973, p. 1213). The process of TFAU according to the invention, using Con-A agarose affinity gel, is generally applicable to the separation of glycoproteins from non-glycoproteins.

The filtration membrane for use in the tangential flow ultrafiltration is selected so that the particles of the affinity substance, and, therefore, their complexes with specifically bound components, are non-filterable, while the components of the mixture to be separated are readily filterable. It is a feature of this process that two or more simple or affinity gel ultrafiltration steps can be combined serially on a continuous-flow basis to achieve complex separations.

The membranes useful in this process of tangential flow ultrafiltration in the present invention are generally as described in the article by F. Raymond Gabler, previously cited. They are generally synthetic membranes of either the microporous (MF) type, the ultrafiltration (UF) type or the reverse osmosis (RO) type. An MF type has pore sizes typically from 0.1 to 10 micrometers, and can be made so that it retains all particles larger than the rated size. UF membranes have smaller pores and are characterized by the size of the globular protein that will be retained. They are available in increments from 1,000 to 1,000,000 nominal molecular weight (dalton) limits, corresponding approximately to 0.001 to 0.05 micrometers. RO membranes are capable of retaining even smaller components, and have effective pore sizes in the range 0.0005 to 0.001 micrometers. For most applications in separation of biological macromolecules, these pore sizes are too small, and will not allow passage even of non-gel-bound macromolecules. Ultrafiltration membranes are most commonly suitable for use in the present invention. UF membranes are normally asymmetrical with a thin film or skin on the upstream surface which is responsible for their separating power. They are commonly made of synthetic polymer films, e.g. polysulfone.

Membrane filters for tangential flow ultrafiltration are available as units, of different configurations depending upon the volumes of liquid to be handled, and in a variety of pore sizes. Particularly suitable for use in the present invention, on a relatively large scale, are those known and commercially available as Millipore Prostack tangential flow ultrafiltration units.

More specifically, according to a first process for separating/purifying native hemoglobin from a hemoglobin-containing solution or mixture, for example, a red blood cell lysate, the process of the invention is as follows. First, a simple tangential-flow filtration step, using a membrane of approximately 100 kilo-dalton cut-off pore size, separates the red cell stroma and large cytoplasmic structures from the cytoplasmic proteins including hemoglobin. These proteins are then mixed with a polyanion affinity gel, to which hemoglobin specifically binds, and then subjected to a second tangential flow filtration step using the same membrane. Affinity gel-hemoglobin complexes are prevented by their size from passing through the filter, while non-hemoglobin solutes are filtered out.

In a third tangential flow filtration step, the gel-hemoglobin complexes are mixed with a solution containing anionic or polyanionic molecules, sucn as ATP, phosphate or sodium chloride, which compete with the polyanion originally bound to the gel for binding to the hemoglobin. Hemoglobin is freed from the gel and passes through the filter. This final filtration step yields pure hemoglobin. The gel can then be reused.

In a second process for separating/purifying modified hemoglobin from a reaction mixture containing chemically modified hemoglobin as well as residual unmodified hemoglobin, due to the incomplete nature of chemical modification reaction, the unmodified hemoglobin must be removed before the solution can be considered for infusion, for example, ATP-hemoglobin or as further modified for use as blood substitute as in the case of polymerization of purified PLP-Hb. To achieve this, the reaction mixture is subjected to tangential flow filtration in the presence of a polyanion affinity gel. Unmodified hemoglobin whose polyanion binding site is unoccupied can bind to the gel and is, therefore, prevented from passing through the filter due to its large molecular size. Modified hemoglobin, whose polyanion binding site is by definition covalently occupied by the modifying agent, cannot bind to the gel and is a small enough molecule to pass tnrough the filter. This yields pure modified hemoglobin which can be used immediately as an acellular oxygen-carrier or subjected to further modification, e.g. polymerization or crosslinking to various biopolymers. It is important that the incompleteness of subsequent modification reactions is not essential, since the product purified by the above process is free of native hemoglobin, which poses the greatest problems in an intravascular solution. The unmodified hemoglobin can subsequently be recovered from the gel by adding a competing anion as in the first process for recycling through the modification process, and the gel can be reused.

The process of the present invention is well adapted for use on a commercial and semi-commercial scale, as described in more detail below. It can be run semi-continuously, i.e. on a continuous-flow basis of solution containing the desired biological macromolecule bound to the affinity gel, past a tangential flow filter, until an entire, large batch has thus been filtered, followed by a stage of continuous flow separation of gel from desired biological macromolecule. Washing stages can be interposed between the filtration stages. Then fresh batches of solution can be treated. In this way, a continuous, cyclic process can be conducted, to give large yields of desired product, in acceptably pure form, in relatively short periods of time. The unique features of affinity gel with its ability to provide highly selective separation of biological macromolecules, but only previously used in chromatographic mode, have been combined with the unique features of tangential flow ultrafiltration with its ability to provide continuous filtration of solids-containing solutions without filter clogging, to provide a unique and highly advantageous process for the separation and purification of biological macromolecular reaction products for use on a continuous basis and a commercial scale. Moreover, the process is of very wide applicability. Whilst it shows great promise is application to hemoglobin and hemoglobin derivatives, it is applicable to a wide range of biological macromolecules, e.g. proteinaceous products of fermentation witn natural or genetically engineered microorganisms, high molecular weight antibiotics, cellular secretions, etc.

EXAMPLE 1

Stroma-free hemoglobin (SFH) was purified using a tangential flow affinity ultrafiltration (TFAU) technique.

SFH was prepared by a modified method of Rosenbery et al. (T. L. Rosenbery, J. F. Cheu, M. M. L. Lee, T. A. Moulton and P. Onigman, J. Biochem. Biophys. Methods, 4, 39–48, 1981) AGATP gels were prepared by a modified method of Lamed and Oplatka (R. Lamed and A. Oplatka, Biochemistry, 13, 3137–3142, 1974).

The filtration apparatus used was an Amicon stir cell witn a DIAFLO ultrafiltration membrance, molecular weight cut-off 100 kilodaltons. This apparatus has a top valved inlet for addition of liquid reagents, a top valved gas inlet for applying gas pressure, a generally cylindrical body, an ultrafiltration membrane mounted generally horizontally as the bottom wall of the body, and a fluid receiving chamber and radial liquid outlet therefrom, below the membrane. There is provided a rotary stirrer within the body, in the form of a flat paddle with planar, perpendicular blade faces just above the level of the membrane, and magnetically operated from outside the cell. Thus, when the stirrer rotates, it causes the liquid contents within the cell body to move continuously across the surface of the membrane, in tangential flow mode. Positive pressure of gas, normally nitrogen, applied through the top gas inlet, causes tangential flow ultrafiltration to be effected through the membrane.

Figure 1A:
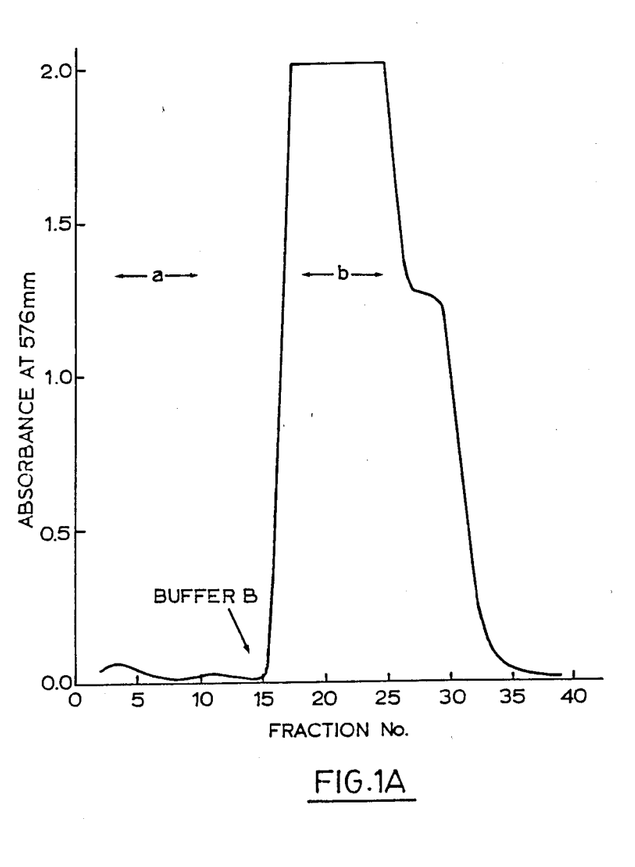
FIG. 1A is a graph which illustrates the Tangential Flow Ultra Filtration (TAFU) profile of stroma-free hemoglobin (SFH) in the presence of agarose-ATP (AGATP) gel, derived from Example 1 below.

In this experiment, a filtration rate of 2 ml/minute, temperature 4° C. and positive nitrogen pressure of 50 psi were employed. Initially, the cell is charged with AGATP and SFH, in a 50 mM Bis-Tris aqueous buffer, ph 7. The SFH binds to the gel to produce a red gel. The filtrate issuing from the bottom of the cell is collected in successive, separate fractions, and spectrometrically analysed for presence of the characteristic hemoglobin red colour (absorbance at 576 nm). The results are illustrated graphicaly on FIG. 1A. In section (a) of the graph, substantially all hemoglobin is retained by the gel, early minor peaks of unbound hemoglobin-containing impurity being shown, and by fraction fifteen, virtually none appears in the filtrate showing that it has all been retained on the affinity gel or removed from the gel vicinity by tangential flow ultrafiltration.

After collection of fifteen fractions, by which time the filtrate was colourless, a competing affinity ligand (Buffer B) was added to the cell through the top liquid inlet, e.g. 10 mM of ATP or 150 mM NaCl, as a buffer of 50 mM Bis-Tris pH 7.0. This displaces the hemoglobin from the gel so that it instantly appears in pure form in the filtrate from the cell by tangential flow ultrafiltration, as shown in section (b) of FIG. 1A.

EXAMPLE 2

Chemically modified pyridoxal phosphate-modified hemoglobin (PLP-Hb) was separated from unmodified stroma-free hemoglobin by tangential flow affinity ultrafiltration.

Figure 1B:
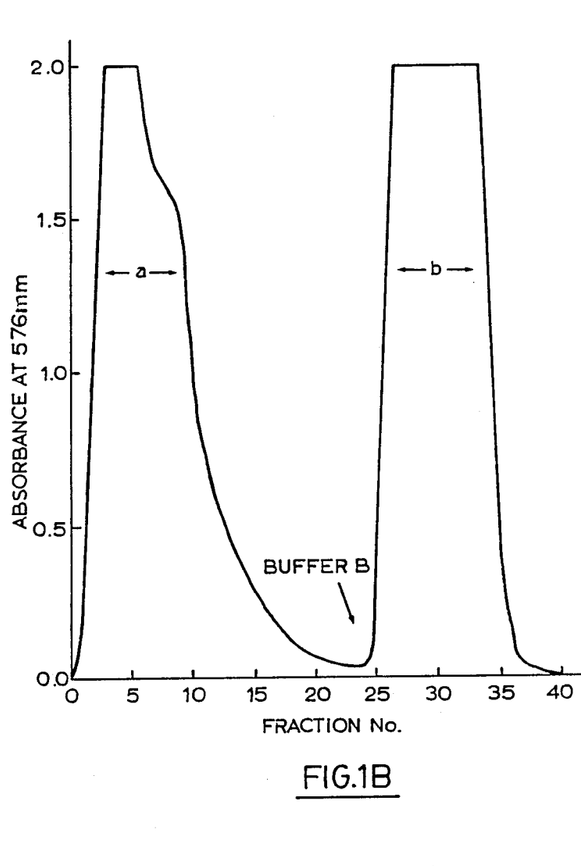
FIG. 1B is a graph which illustrates the TAFU profile of a reaction mixture containing pyridoxal phosphate modified SFH in the presence of AGATP gel, derived from Example 1 below.

PLP-Hb was prepared by the method F. DeVenuto and A. Zegna (J. Surg. Res. 34, 205–212, 1983). Stroma-free hemoglobin and AGATP gels were prepared as previously indicated. The apparatus and filtration conditions were as described in Example 1. The reaction mixture of PLP-Hb (about 75% yield) containing SFH (or residual unmodified Hb) was introduced into the cell and subjected to tangential flow ultrafiltration in the presence of the AGATP. As illustrated in FIG. 1B, the purification of this mixture gives two major fractions, indicated as peaks a and b. PLP-Hb, the reaction product, with its diphosphoglycerate binding site occupied, can no longer bind to the AGATP gel, so that it immediately passes tnrough the membrane by tangential flow affinity ultrafiltration, to give peak a, whilst the unmodified Hb and SFH, i.e. the unreacted hemoglobin starting materials, bind to the gel and do not pass through the filter. When all the PLP-Hb has passed through the filter, as denoted by the colourless nature of the filtrate then being obtained, Buffer B, as described in Example 1, is added to the cell. This effectively detaches the SFH and unmodified hemoglobin from the gel, so that it now passes through the filter, as denoted by peak b. Note the similarity to the SFH peak in FIG. 1A.

This example illustrates the use of the process of the present invention to effect a clean separation of a modified hemoglobin product from unmodified hemoglobin, when hemoglobin has been modified to form a blood substitute or an acellular oxygen-carrying compound.

FIG. 2 shows the high pressure liquid chromatography (HPLC) analysis of the SFH, PLP-Hb reaction mixtures, AGATP retained and unretained fractions of the reaction mixture. FIGS. 2A–2D are chromatograms of samples of (A) SFH (50 micrograms), (B) PLP-Hb reaction mixture (100 micrograms), (C) retained fraction (5.0 micrograms), i.e. peak b from FIG. 1B, and (D) unretained fraction (50 micrograms) (peak a from FIG. 1B) eluted from a HR 5/5 Mono S ion-exchange column (Pharmacia). In each case, the solid line indicates the elution of the hemoglobin solutions by buffer A (10 mM malonate, pH 5.7) followed by a linear gradient of buffer B (Buffer A plus 0.3M lithium chloride, pH 5.7, broken line). Experimental conditions were: flow rate 0.5 ml/min, temperature 22° C., using a Pharmacia HPLC chromatographic system with Model LCC-500 controller.

Figure 2A:
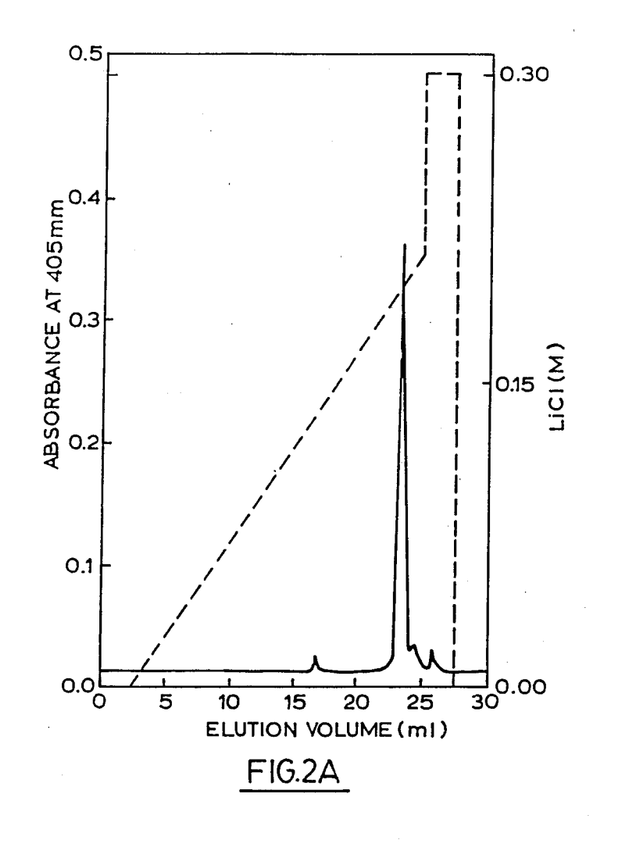
FIGS. 2A and 2D are a series of graphs which characterize purified hemoglobin fractions by High Performance Liquid Chromatography (HPLC), derived from Example 1 below.
Figure 2B:
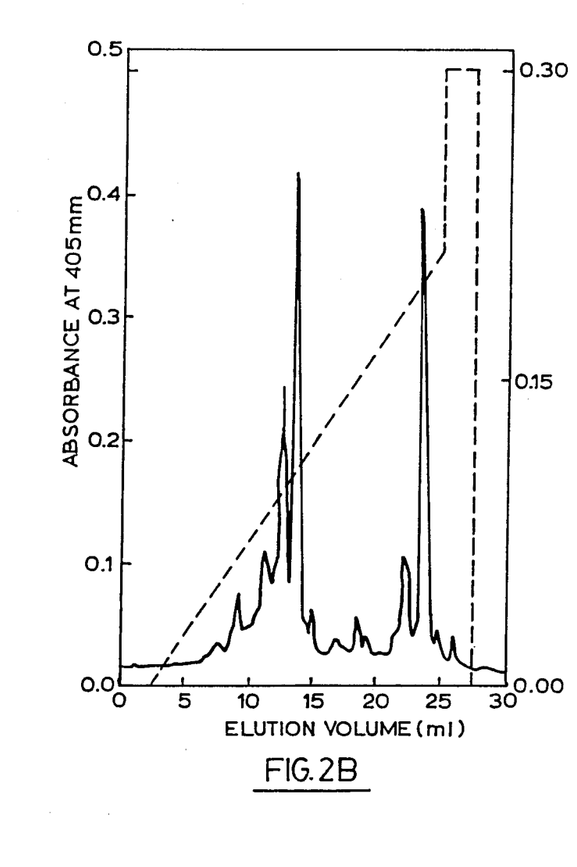
Figure 2C:
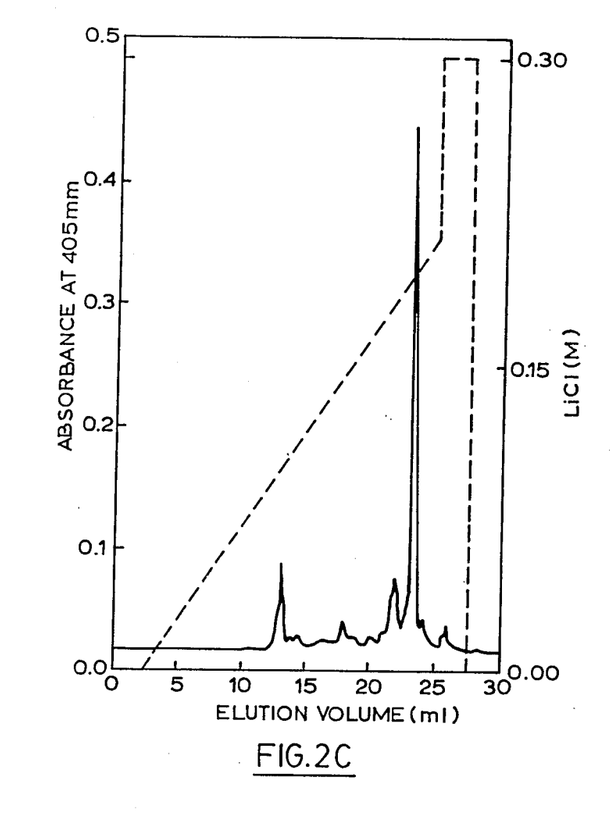
Figure 2D:
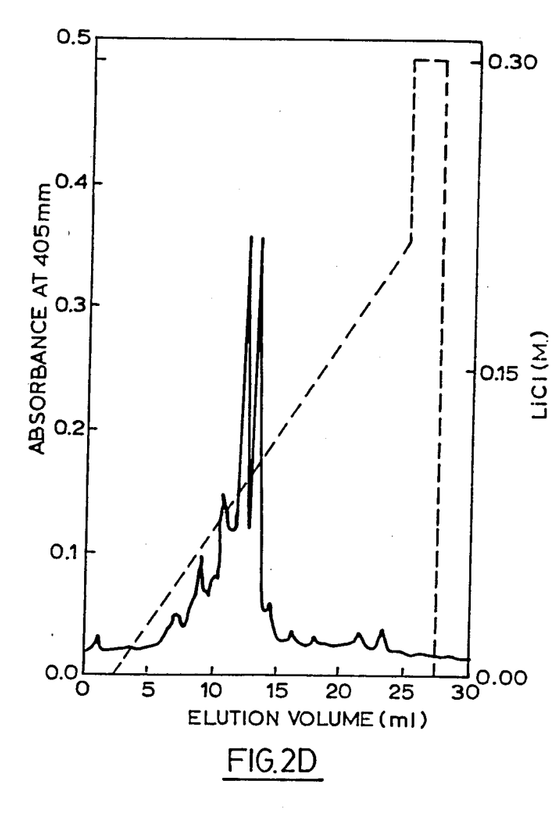

Pure SFH gives predominantly a single peak, as shown in FIG. 2A. The SFH PLP-Hb reaction mixture gives two clusters of peaks, as shown in FIG. 2B. The second peak occurring at high salt gradient compares with SFH in FIG. 2A and the first peak(s) eluting at lower concentrations of buffer B probably contain various species of PLP-Hb (R. Benesch, R. E. Benesch and Suzanna Kwong, J. Biol. Chem., 275, 1320–1324, 1982). Following TFAU of the reaction mixture as described above, the retained and unretained fractions were similarly analysed by HPLC. FIG. 2C relates to the retained fraction, peak b of FIG. 1B, and is similar to SFH in FIG. 2A and is predominantly SFH. The unretained fraction, FIG. 2D, is free of SFH and contains primarily PLP-Hb species. Note the similarity of these peaks to the first peak(s) in FIG. 2B. Thus the process TFAU as described in these examples can produce highly purified PLP-Hb.

Figure 3:
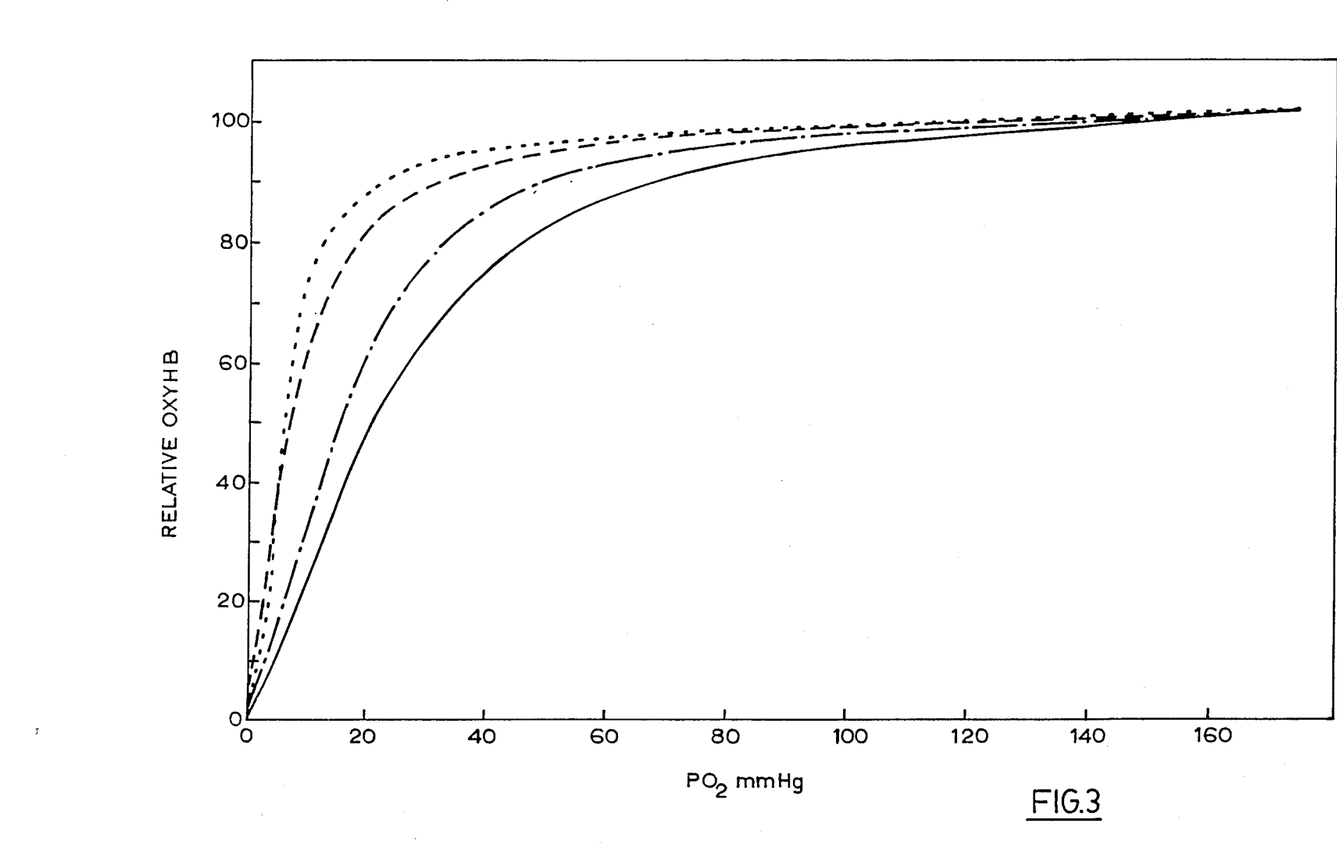
FIG. 3 is a graph which illustrates the effects of TFAU on the oxygen binding affinity of hemoglobin fractions purified according to the invention, and derived from Example 1 below.

FIG. 3 illustrates the oxygen dissociation curves of PLP-Hb reaction mixture (—.—.—) and TFAU-separated fractions a, PLP-Hb, (—), b, unmodified Hb, (— — —) and SFH (.....) in 50 mM Bis-Tris buffer at 37° C. Curves were obtained using a Hem-O-Scan oxygen dissociation analyzer.

These oxygen dissociation curves indicate that the partial pressure of oxygen ($P_{50}$) at which 50% of the hemoglobin is oxygenated is affected by the TFAU purification. TFAU-purified PLP-Hb has a lower $P_{50}$(21 mmHg) than the reaction mixture (15 mmHg). The retained fraction ($P_{50}=7$ mmg) is similar to that of SFH ($P_{50}=6$ mmHg). Thus TFAU effectively separates PLP-Hb from SFH in the reaction mixture, as characterized by HPLC analysis and oxygen-releasing efficacy (i.e. lower $P_{50}$). In addition, removal of unmodified SFH may have other beneficial effects, e.g. increased intravascular half-life and reduced vasoconstrictive activity of the hemoglobin-based blood substitute.

It must be pointed out that any modified hemoglobin, such as ATP-Hb or glyoxylate-Hb, can be purified by this technique. In addition, this method is a general purification technology which may be applied to other biomacromolecules of interest.

Another aspect of this purification method is that it uses a 100 kilodalton cutoff membrane filter which allows hemoglobin (diameter 5 nm) to pass through, it may be capable of excluding infectious agents such as hepatitis B virus (42 nm diameter) and the AIDS virus, HTLV-III (100 nm diameter). Thus the blood substitute prepared from TFAU purified hemoglobin has the potential to be free of blood-borne viral disease.

Figure 4:
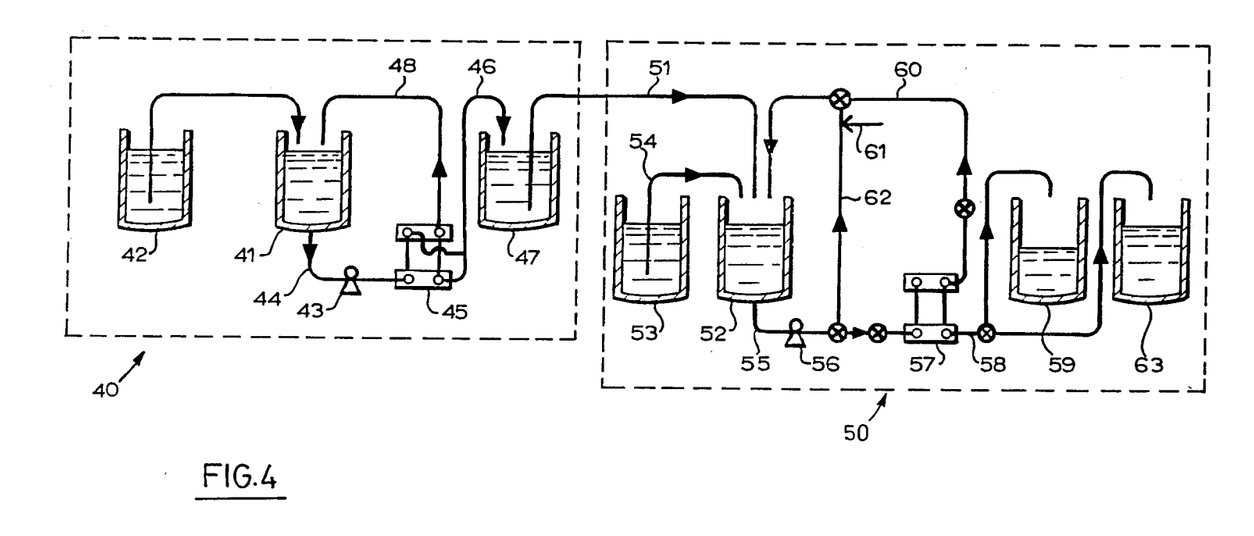
FIG. 4 is a diagrammatic process flow sheet of a commercial or semi-commercial facility for putting the present invention into practice.

With reference to FIG. 4 of the accompanying drawings, this illustrates diagrammatically, in flow sheet form, a semi-commercial or commercial facility for purification of a biological product such as hemoglobin, according to the process of the present invention. The process includes a first stage 40 in which red blood cells are washed, lysed and filtered to remove cell residues and produce stroma-free hemoglobin (SFH). The process also includes a second stage 50, operated successively to first stage 40, in which the SFH is purified to obtain pure hemoglobin (Hb).

In the first stage 40, the starting material, red blood cells from which the hemoglobin is to be extracted and purified, is stored in reservoir 41 in which it can be washed and lysed with appropriate solution from vessel 42 in the known way. Then it is pumped by means of pump 43 through outlet line 44 to the inlet side of a Millipore Prostack tangential flow filter unit 45. The filtrate, namely SFH, is then fed from the outlet side of filter unit 45 via line 46 to holding vessel 47, whilst the portion of the material which does not pass through the filtration membrane of unit 45 (i.e. the retentate) is recirculated via line 48 to reservoir 41 for recirculation through the filter unit 45. Washing solution from vessel 42 can be used to wash reservoir 41 and filter unit 45, after a batch of red blood cell ghosts have thus been washed and the lysate moved onto holding vessel 47.

In the second stage 50, the combined process of affinity chromatography and tangential flow ultrafiltration (TFAU) is employed, to produce pure hemoglobin. From the holding vessel 47 of the first stage 40, a batch of the SFH is fed, in a first phase of operation, via line 51 to a reaction vessel 52. There is provided a container 53 of washing solution which can be fed via line 54 to reaction vessel 52 as and when desired, during washing phases described below. The reaction vessel 52 contains an affinity gel, namely an agarose-ATP affinity gel as described in U.K patent application Ser. No. 8,615,675, filed June 26, 1986. In a first phase of operation of the process stage 50, this gel selectively binds to the hemoglobin in reaction vessel 52. The liquid mixture containing the hemoglobin-gel complex is then fed via outlet line 55 by means of pump 56 to the inlet side of a Millipore Prostack tangential flow filter unit 57, essentially similar to that used in the first stage 40. Here, the impurities including the modified hemoglobins and the like which have not selectively bound to the gel are passed through the filter as filtrate and fed out of the filter unit 57 via filtrate line 58 to receiving vessel 59, for discard or further utilization. Meanwhile, the Hb-gel complex does not pass the filter and is returned as retentate via retentate line 60. Next, in a second constant volume washing phase, the gel-Hb complex in reaction vessel 52 and filter unit 57 are washed with solution from container 53, the solution being chosen so that it does not chemically dislodge the Hb from the gel in reaction vessel 52. The wash solution passing the filter may be added to the filtrate in the first receiving vessel 59.

When the entire batch of SFH from reaction vessel 52 has thus been filtered and washed, reaction vessel 52 contains gel-hemoglobin complexed perhaps mixed with some unreacted gel, but substantially totally free of other impurities. Now it is required to remove the Hb from the gel and recover the gel for reuse with another batch of SFH. Then, in a third phase, salt solution, namely sodium chloride solution, is fed into reaction vessel 52 from inlet port 61, located in by-pass line 62, and retentate line 60. In reaction vessel 52, hemoglobin is replaced on the ATP gel by sodium ions, and the hemoglobin in solution, along with the gel, passes via outlet line 55 to filter unit 57, through which it passes as filtrate and is led via filtrate line 58 to second receiving vessel 63. The gel, meanwhile, exits the filter uit 57 via retentate line 60 to return to reaction vessel 52, where it is ready for re-use with another batch of SFH from the first stage 40. A further constant volume washing cycle, using solution from vessel 53, must be used before another batch of SFH is reacted to restore the gel binding capacity, to minimize line contamination, filter contamination and the like. Of course, appropriate valve controls are included, generally as illustrated, to allow the process to be operated in the different phases and cycles with minimum manual adjustments. The by-pass line 62 may equipped with appropriate controllers, analytical instruments, sensors, samples, degassers and the like, to allow satisfactory monitoring and control of the process as a whole.

Such a facility is readily capable of producing up to 2,400 units of hemoglobin per 8-hour run. It is, nevertheless, simple and inexpensive to construct and operate, and capable of being built as a prefabricated or mobile facility, at a location of immediate need for blood processing.

Moreover, the facility generally as illustrated is capable of extracting and purifying a wide variety of biological molecules of interest, from solution in which they are contained, in high or low concentration, such as fermentation solutions. In the first stage 40, all debris, yeast residues, etc. from a fermentation process mixture can be removed, to give a filtrate containing the desired product, but still in impure form. This filtrate is then moved onto the second stage where the mixture contacts an appropriately chosen affinity gel to which the desired product selectively binds. Then the mixture is subjected to tangential flow affinity ultrafiltration (TFAU) to remove the non-bound impurities, the gel is returned to the reaction vessel and the desired product is removed from the gel, e.g. by salt elution and the mixture is again subjected to tangential flow ultrafiltration to separate the desired product, in pure form, from the gel.

By suitable adaptation of the operating stages and cycles, the facility as generally illustrated is also capable of handling products prepared by so-called "negative affinity absorption", i.e. a process in which a desired biological substance is separated from an undesired substance by use of an affinity gel which is selective to bind the undesired substance. Then, the desired substance in the first phase of the second stage is recovered as the filtrate from the tangential flow ultrafiltration unit 57, in first receiving vessel 59. The undesired substance or impurity is subsequently eluted from the gel and separated therefrom by the tangential flow affinity filtration unit 57 in a second phase, and the gel thus prepared ready for re-use. Example 2 described above, in which pyridoxal hemoglobin PLP-Hb is separated from unmodified hemoglobin is a specific example of the use of the process of the invention in negative affinity absorption mode.

I claim:

1. A process of separating a first biological macromolecule from a second biological macromolecule which comprises treating a mixture containing both of said first and second biological macromolecules with a macromolecular affinity substance having ligands which endow biological binding specificity to one of said first and second macromolecules but not to the other thereof, and subsequently subjecting the mixture containing the affinity substance-bound macromolecules to tangential flow ultrafiltration, so as to obtain affinity substance-bound macromolecules in the retentate of said ultrafiltration and non-affinity substance-bound macromolecules in the filtrate of said ultrafiltration.

2. The process of claim 1 wherein one of said first biological macromolecule and said second biological macromolecule is hemoglobin or a derivative thereof.

3. The process of claim 2 wherein the affinity gel is an agarose gel having a selective affinity binding anion attached thereto through a space or chemical group of at least 5 angstroms.

4. The process of claim 3 wherein the selective affinity binding anion is an organic phosphate, a nucleic acid phosphate, an inositol phosphate, a carbohydrate phosphate, a carbohydrate sulfate, a carbohydrate monocarboxylate, a carbohydrate polycarboxylate or diphosphoglycerate.

5. The process of claim 1 wherein, subsequent to the tangential flow ultrafiltration, the affinity-substance-bound macromolecules in the retentate are chemically displaced from binding with the macromolecular affinity substance, and the mixture of macromolecular affinity substance and macromolecules so formed is subjected to tangential flow ultrafiltration to separate the macromolecular affinity substance therefrom.

6. The process of claim 5 wherein the macromolecular affinity substance is subsequently recycled to bind selectively to one of said first and second macromolecules from another batch of mixture containing them.

7. The process of 1 wherein the macromolecular affinity substance is an affinity chromatographic gel.

8. The process of claim 7 wherein the affinity gel is an agarose gel or a silica gel.

9. The process of claim 8 wherein said first and second biological macromolecules are hemoglobin and hemoglobin derivatives.

10. The process of claim 8 wherein the first and second biological macromolecules are a glycoprotein and a non-glycoprotein.

11. The process of claim 10 wherein the affinity gel is agarose bound to concanavalin-A.

12. The process of claim 1 wherein the macromolecular affinity substance is a soluble ligand-binding macromolecular substance.

13. The process of claim 1 wherein said first and second biological macromolecules are hemoglobin and hemoglobin derivatives.

14. The process of claim 1 wherein one of said first biological macromolecule and said second biological macromolecule is oxyhemoglobin.

* * * * *